US 9,603,986 B2

(12) United States Patent
Kusters et al.

(10) Patent No.: US 9,603,986 B2
(45) Date of Patent: Mar. 28, 2017

(54) DEVICE AND METHOD FOR PROCESSING AND PRODUCING AUTOLOGOUS PLATELET-RICH PLASMA

(71) Applicants: Benjamin E. Kusters, Pleasant Prairie, WI (US); Christopher J. Wegener, Libertyville, IL (US); Kyungyoon Min, Kildeer, IL (US)

(72) Inventors: Benjamin E. Kusters, Pleasant Prairie, WI (US); Christopher J. Wegener, Libertyville, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 358 days.

(21) Appl. No.: 14/014,542

(22) Filed: Aug. 30, 2013

(65) Prior Publication Data

US 2015/0060363 A1     Mar. 5, 2015

(51) Int. Cl.
   *B01D 63/16*     (2006.01)
   *A61M 1/34*      (2006.01)
   (Continued)

(52) U.S. Cl.
   CPC ........ *A61M 1/3496* (2013.01); *A61M 1/0218* (2014.02); *A61M 1/265* (2014.02);
   (Continued)

(58) Field of Classification Search
   CPC .. A61M 1/0218; A61M 1/265; A61M 1/3496; A61M 2205/103; A61M 2205/75;
   (Continued)

(56) References Cited

U.S. PATENT DOCUMENTS

| 4,871,462 A | 10/1989 | Fischel et al. |
| 5,194,145 A | 3/1993 | Schoendorfer |

(Continued)

FOREIGN PATENT DOCUMENTS

| WO | WO 92/10275 A1 | 6/1992 |
| WO | WO 2011/119535 A1 | 9/2011 |
| WO | WO 2012/125457 A1 | 9/2012 |

OTHER PUBLICATIONS

Extended European Search Report, Appl. No. 13189038.6-1403; dated Dec. 5, 2014.

*Primary Examiner* — Dirk Bass
(74) *Attorney, Agent, or Firm* — Cook Alex Ltd.

(57) ABSTRACT

A system and method are provided, including an integrated single-use kit, for processing whole blood to produce platelet rich plasma. A two stage spinning membrane separator, has a first stage for receiving whole blood and separating substantially all red blood cells from plasma and platelets, and a second stage for further separating platelet rich plasma from plasma. A first waste container is in fluid communication with the first stage of the separator for receiving separated red blood cells, while a second waste container is in fluid communication with the second stage of the separator for receiving separated plasma. An outlet line is in fluid communication with the second stage of the separator for receiving platelet rich plasma, and a reinfusion container is removably connected to the outlet line for receiving platelet rich plasma from the second stage of the separator.

15 Claims, 4 Drawing Sheets

(51) Int. Cl.
*A61M 1/26* (2006.01)
*A61M 1/02* (2006.01)

(52) U.S. Cl.
CPC ....... *B01D 63/16* (2013.01); *A61M 2205/103* (2013.01); *A61M 2205/75* (2013.01); *B01D 2317/02* (2013.01); *B01D 2319/02* (2013.01); *B01D 2319/06* (2013.01)

(58) Field of Classification Search
CPC ............ B01D 2317/02; B01D 2319/02; B01D 2319/06; B01D 63/16
USPC ............................................ 210/321.68, 651
See application file for complete search history.

(56) References Cited

U.S. PATENT DOCUMENTS

| | | | |
|---|---|---|---|
| 6,709,413 B1 * | 3/2004 | Chance | A61K 35/16 210/782 |
| 7,220,354 B2 | 5/2007 | McLaughlin et al. | |
| 7,531,094 B2 | 5/2009 | McLaughlin et al. | |
| 2003/0146154 A1 * | 8/2003 | Moriarty | A61M 1/16 210/646 |

* cited by examiner

DEVICE AND METHOD FOR PROCESSING AND PRODUCING AUTOLOGOUS PLATELET-RICH PLASMA

FIELD OF THE DISCLOSURE

The present disclosure relates to blood processing systems and methods. More particularly, the present disclosure relates to systems and methods for processing and producing platelet-rich plasma from blood, or from a fluid containing blood plasma and platelets, for therapeutic infusion.

DESCRIPTION OF RELATED ART

A wide variety of blood processing systems make it possible to separate and collect particular blood constituents from a blood source. Typically, in such systems, whole blood is drawn from a blood source, the particular blood component or constituent is separated, removed, and collected, and the remaining blood constituents then may be returned to the blood source, or otherwise disposed of.

Whole blood may be separated into its constituents by employing any of a number of methods and systems. For example, it is known to use a spinning porous membrane to separate plasma from whole blood. Spinning membrane separators have been found to provide excellent filtration rates, due primarily to the unique flow patterns ("Taylor vortices") induced in the gap between the spinning membrane and the shell. The Taylor vortices help to keep the red blood cells from depositing on and fouling or clogging the membrane.

A well-known plasmapheresis device is the Autopheresis-C® separator sold by Fenwal, Inc. of Lake Zurich, Ill. A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, move to the exit region between the spinner and the shell and then are typically returned to the donor.

To avoid potential contamination, the blood is preferably contained within a preassembled, sterile fluid flow circuit or system during the entire separation process. Typical spinning membrane blood processing systems thus include a permanent, reusable module or assembly containing the durable hardware (drive system, pumps, valve actuators, programmable controller, and the like) that spins and controls the processing of the blood and blood components through a disposable, sealed, and sterile flow circuit that includes a spinning membrane separator that is mounted in cooperation on the hardware.

One use of separated blood components is platelet-rich plasma (PRP) therapy. PRP therapy typically involves first withdrawing approximately 60-120 ml of whole blood from the patient using a syringe. The whole blood is then processed to produce a low volume of plasma containing a high concentration of platelets. The PRP is then injected back into the patient at the locus of the wound or injured body part to stimulate repair and regeneration of the body's tissues.

Key benefits of platelet-rich plasma are the autologous derivation of growth factors and its minimal adverse-effect profile. At this time, the regenerative, inflammatory-modulating, and wound healing hastening abilities of platelet-rich plasma are primarily being applied to recalcitrant circumstances, but other therapeutic uses for platelet-rich plasma, such as its applicability in treating musculoskeletal and vascular pathologies, are also being explored.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a disposable flow circuit is provided for use in combination with a fluid processing device for isolating platelet-rich plasma from a fluid containing red blood cells, plasma and platelets. More particularly, a closed, preassembled and pre-sterilized kit for batch processing of blood to produce a concentrated platelet product is provided that comprises a inlet into which blood may be flowed. A two-stage separation device is provided in which the first stage comprises a first gap defined between spaced-apart first inner and first outer relatively rotatable surfaces, with the first gap being in fluid communication with the inlet, and at least one of the first inner and first outer surfaces comprising a first filter membrane that substantially blocks red blood cells from passing therethrough, while allowing platelets and plasma to pass therethrough. The second stage comprises a second gap that is defined between spaced-apart second inner and second outer relatively rotatable surfaces, with at least one of the second inner and second outer relatively rotatable surfaces comprising a second filter membrane that substantially blocks platelets from passing therethrough while allowing plasma to pass therethrough. The apparatus is configured so that the second gap receives plasma and platelets passing through the first filter membrane. A drive assembly is provided for causing relative rotational movement between the first inner and first outer surfaces and between the second inner and second outer surfaces such that plasma and platelets pass through the first filter membrane and plasma passes through the second filter membrane to provide a concentrated platelet product in the second gap. An outlet communicates with the second gap for withdrawing concentrated platelet product from the second gap.

In another aspect, the apparatus further comprises a container attached to the outlet for receipt of the concentrated platelet product. Preferably, the collection container comprises an injection device, such as a syringe, from which the concentrated platelet product can be reinfused into the patient. Additionally, the first filter membrane preferably has an average pore size of from 4 um to 5 um and the second filter membrane has an average pore size of approximately 0.65 um.

In another aspect, an integrated single-use kit forming a closed system for processing whole blood to produce platelet rich plasma is provided. The kit comprises a two stage spinning membrane separator, with a first stage for receiving whole blood and separating substantially all red blood cells from plasma and platelets, and a second stage in fluid communication with the first stage for further separating platelet rich plasma from plasma. An inlet is provided for flowing whole blood to the first stage of the separator by means of a pump for applying pressure to whole blood in the inlet line. A first waste container in fluid communication with the first stage of the separator may be provided for receiving separated red blood cells, while a second waste container in fluid communication with the second stage of the separator may be provided for receiving separated plasma. An outlet in fluid communication with the second stage of the separator is provided for receiving platelet rich plasma, and a reinfusion container may be removably connected to the outlet line for receiving platelet rich plasma from the second stage of the separator, and the inlet further comprises a connector for attaching a collection syringe thereto.

Preferably, the kit comprises first and second spinning membrane separators, each having an inlet and first and second outlets, the first outlet of the first spinning membrane separator being in fluid communication with the first waste container and the second outlet being in fluid communication with the inlet of the second spinning membrane separator, the first outlet of the second spinning membrane separator being in fluid communication with the outlet line and the second outlet being in fluid communication with the second waste container. The first stage preferably comprises a filter membrane having an average pore size of from 4 um to 5 um, while the second stage preferably comprises a filter membrane having an average pore size of approximately 0.65 um.

In a further aspect, the system comprises a collection syringe associated with a first syringe pump for expressing the whole blood from the collection syringe to the first stage of the two stage spinning membrane separator, and the reinfusion container comprises a syringe is associated with a second syringe pump for withdrawing platelet rich plasma from the second stage of the two stage spinning membrane separator through the outlet line and into the reinfusion syringe.

In a further aspect, the two stage separator comprises a first stationary membrane separator and a second spinning membrane separator mounted interior of the first stationary membrane separator. More specifically, a two-stage system for filtering a cellular suspension is provided that comprises a stationary housing having an inner wall defining a hollow interior; a first generally cylindrical filter membrane and substrate having a hollow interior rotatably fixed relative to the housing and spaced from the inner wall of the housing to define a first gap therebetween; a second generally cylindrical filter membrane and substrate having a hollow interior mounted interior of the first filter membrane and substrate and for rotation relative to the housing and first filter membrane and substrate, the second filter membrane and substrate being spaced relative to the first filter membrane and substrate to define a second gap therebetween; with the housing further having inlet in fluid communication with the second gap and first, second, and third outlets in fluid communication with the first gap, second gap, and hollow interior of the second filter membrane and substrate, respectively; and a motor coupled to the second filter membrane and substrate for rotating the second filter membrane and substrate relative to the housing and first filter membrane and substrate at a rate sufficient to establish Taylor vortices in the second gap. Further, the system preferably further comprises selectively controllable valves associated with each of the first, second, and third outlets of the housing for controlling the direction of flow through the filter membranes.

In another aspect, a method for producing platelet rich plasma for reinfusion to a donor using a kit or apparatus as set forth above is provided. The steps comprise obtaining whole blood from the donor in a collection container; connecting the collection container to the inlet line; flowing whole blood from the collection container through the inlet line to the first stage of the two stage spinning membrane separator; separating red blood cells from platelets and plasma in the first stage; flowing separated platelets and plasma from the first stage to the second stage of the spinning membrane separator; separating platelet rich plasma from plasma in the second stage of the two stage spinning membrane separator; flowing the platelet rich plasma from the second stage of the spinning membrane separator through the outlet line to a reinfusion container; and disconnecting the reinfusion container from the outlet line.

DESCRIPTION OF THE ILLUSTRATED EMBODIMENTS

A more detailed description of the two stage spinning membrane separation system in accordance with the present disclosure is set forth below. It should be understood that description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figures 1, 2:
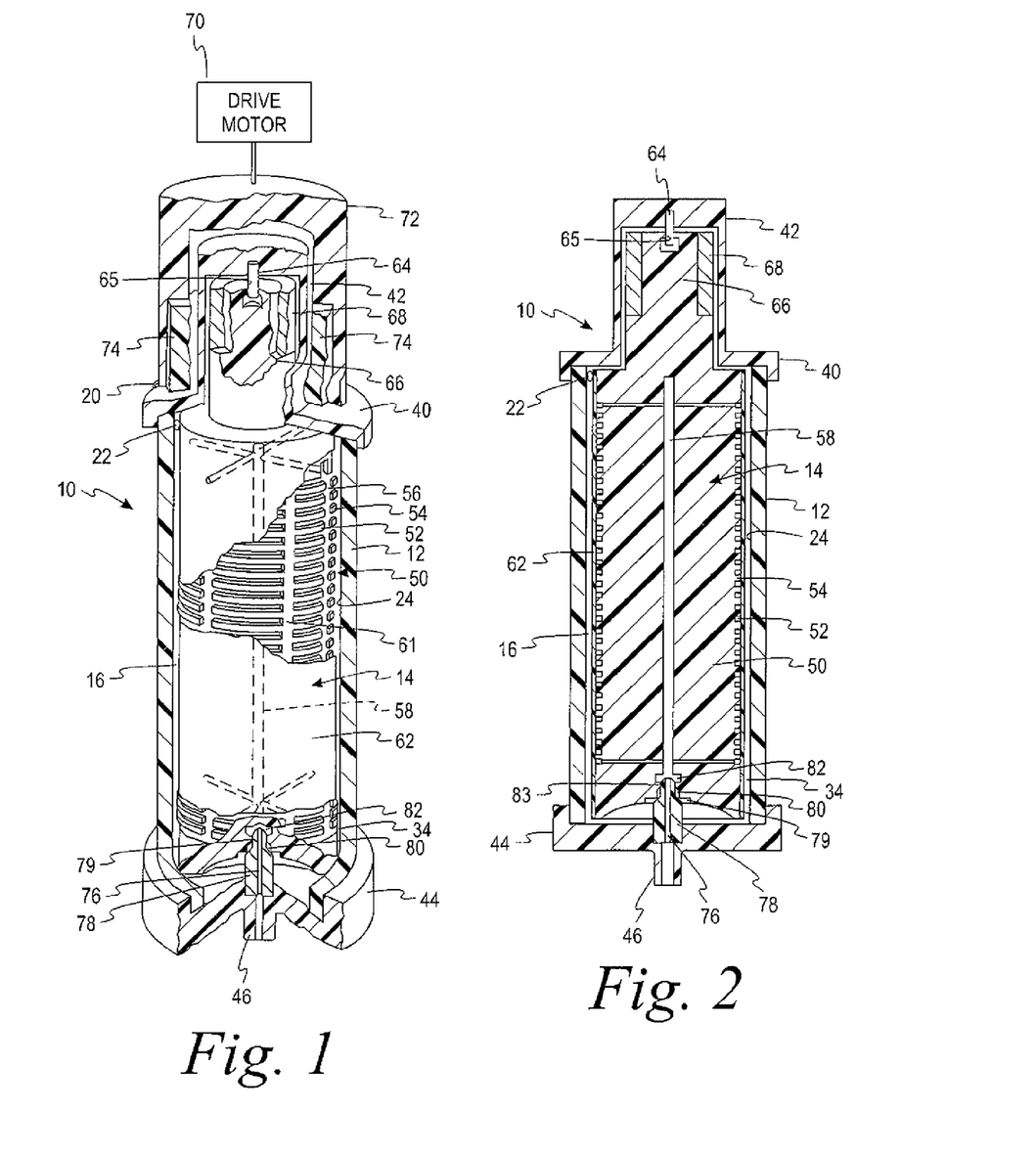
FIG. 1 is a perspective view a spinning membrane separator, in partial cross section and with portions removed to show detail.
FIG. 2 is a longitudinal cross sectional view of the spinning membrane separator of FIG. 1.
Figure 3:
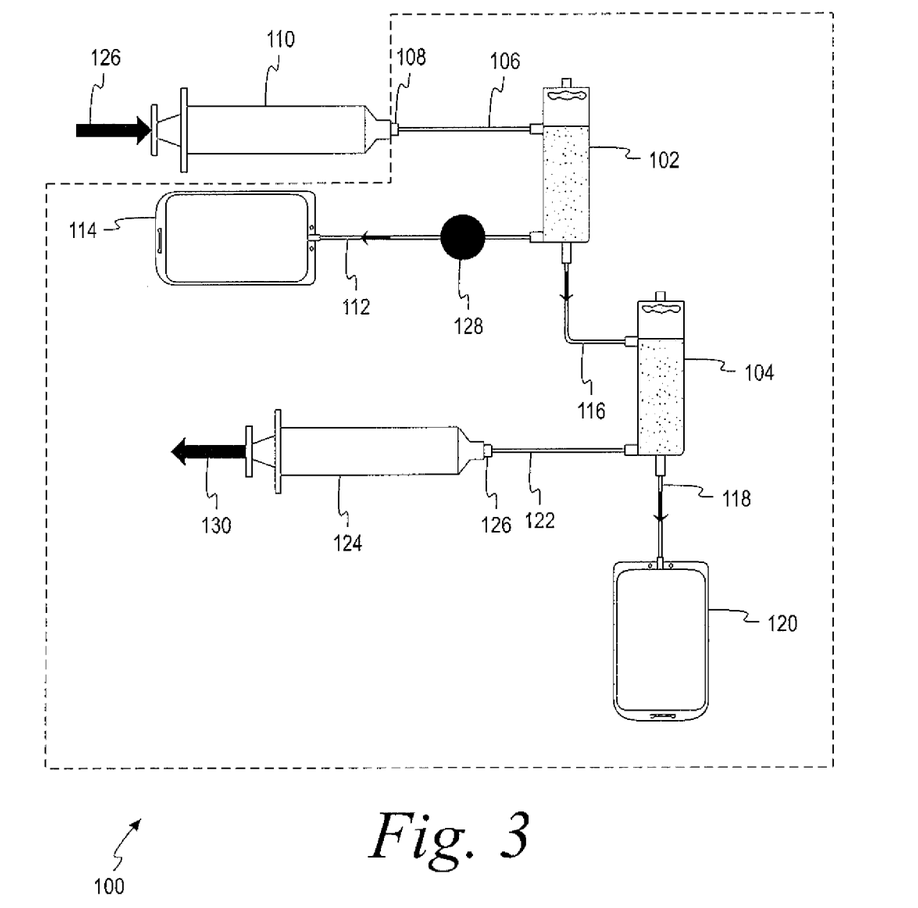
FIG. 3 is a schematic view of a system for isolating platelet-rich plasma in accordance with the present disclosure including a disposable flow circuit incorporating two spinning membrane separators.

Turning to FIGS. 1 and 2, there is seen an exemplary spinning membrane blood separation device, generally designated 10, of the type that may be used in connection with the systems and methods described herein. Such a device forms part of the single use kit of the present disclosure that may additionally include collection containers, waste bags, tubing, etc., as described in greater detail below in connection with FIG. 3. There are also associated pumping, valving, control and instrumentation systems associated with a hardware component of the system, some of which are also shown in FIG. 3.

The spinning membrane separator 10 includes a generally cylindrical housing 12, mounted concentrically about a longitudinal vertical central axis. In one embodiment of the system described herein, two such spinning membrane separators would be used to provide first and second stages of separation. An internal member 14 is mounted concentric with the central axis. The housing and internal member is relatively rotatable. In the preferred embodiment, as illustrated, the housing is stationary and the internal member is a rotating spinner that is rotatable concentrically within the cylindrical housing 12. The boundaries of the blood flow path are generally defined by the gap 16 between the interior surface of the housing 12 and the exterior surface of the rotary spinner 14. The spacing between the housing and the spinner is sometimes referred to as the shear gap. A typical shear gap is approximately 0.025" (0.06 cm) and may be of uniform dimension, for example, where the axis of the spinner and housing are coincident. The sheer gap may also vary tangentially, for example, where the axis of the spinner and housing are offset, or axially. The width dimension of the gap is preferably selected so that at a selected relative rotational speed, Taylor vortices are created on the gap.

The device includes an inlet conduit 20 and an inlet orifice 22, which directs blood into the flow entrance region in a path tangential to the circumference about the upper end of the spinner 14. At the bottom end of the cylindrical housing 12, the housing inner wall includes an exit orifice 34, through which red blood cells would exit after the first stage of separation, and platelet-rich plasma would exit after the second stage.

The cylindrical housing 12 is completed by an upper end cap 40 having an end boss 42, the walls of which are nonmagnetic, and a bottom end housing 44 terminating in a outlet orifice 46 concentric with the central axis through which plasma and platelets would exit after the first stage of separation, and plasma would exit after the second stage.

The spinner 14 is rotatably mounted between the upper end cap 40 and the bottom end housing 44. The spinner 14 comprises a shaped central mandrel or rotor 50, the outer surface of which is shaped to define a series of spaced-apart circumferential grooves or ribs 52 separated by annular lands 54. The surface channels defined by the circumferential grooves 52 are interconnected by longitudinal grooves 56. At each end of the mandrel 50, these grooves 56 are in communication with a central orifice or manifold 58.

In the illustrated embodiment, the surface of the rotary spinner 14 is at least partially, and is preferably substantially or entirely, covered by a cylindrical porous membrane 62. When used for separating red blood cells in whole blood from plasma, as in the first stage of the present method and system, the membrane 62 typically would have an average pore size of from approximately 4 um to 5 um, and is preferably a polycarbonate track etched membrane. If platelet rich plasma is to be separated from plasma, as in the second stage of the present system and method, the membrane 62 typically would have an average pore size of from approximately 0.65 um to 0.8 um, and is preferably a nylon mesh membrane.

The rotary spinner is mounted in the upper end cap to rotate about a pin 64, which is press fit into the end cap 40 on one side and seated within a cylindrical bearing surface 65 in an end cylinder 66 forming part of the rotary spinner 14. The internal spinner or outer housing may be rotated by any suitable rotary drive device or system. As illustrated, the end cylinder 66 is partially encompassed by a ring 68 of magnetic material utilized in indirect driving of the spinner 14. A drive motor 70 exterior to the housing 12 is coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing locks the spinner 14 to the exterior drive, causing the spinner 14 to rotate.

At the lower end of the rotary spinner 14, the central outlet orifice 58 communicates with a central bore 76 in an end bearing 78 that is concentric with the central axis. An end bearing seat is defined by an internal shoulder 80 that forms a lower edge of a central opening 82. The central opening 82 communicates with the plasma outlet orifice 46. If the inner facing surface of the housing is covered entirely or partially by a membrane, a fluid collection or manifold may be provided beneath the membrane to collect the separated fluid, and direct it through a housing outlet (not seen).

Turning to FIG. 3, a single use kit 100 is shown that includes two spinning membrane separators 102 and 104, as described above, to provide two stages of separation of whole blood to produce platelet-rich plasma. The first stage spinning membrane separator 102 separates whole blood into red blood cells and plasma with platelets, while the second stage spinning membrane separator 104 separates the plasma with platelets into platelet-rich plasma and plasma.

The kit 100 includes an inlet line 106 for flowing whole blood into the first stage separator 102. The inlet line 106 includes a connector 108 for attaching a container 110 that holds the whole blood that has been withdrawn from the patient. Preferably, the container 110 comprises a syringe that has been used to draw the patient's blood, and which may be connected to the inlet line 106 by means of, e.g., a luer connector.

A red blood cell line 112 having a collection container 114 attached thereto is provided for flowing separated red blood cells from the first stage separator 102 into the collection container 114. The separated red blood cells received in the collection container 114 are typically considered to be a waste byproduct of processing blood to produce platelet-rich plasma.

The kit further includes an in-process line 116 for flowing separated plasma with platelets from the first stage separator 102 into the second stage separator 104. A plasma line 118 having a collection container 120 attached thereto is associated with the second stage separator 104 for flowing separated plasma from the second stage separator 104 into the collection container 120. The separated plasma received in container 120 is also typically considered to be a waste byproduct when producing plate-rich plasma.

The second stage separator 104 also has a line 122 for flowing platelet-rich plasma into a collection container 124 from which the platelet-rich plasma will be reinfused into the patient. The collection container 120 preferably comprises a syringe that is removably attached to the platelet-rich plasma line 118 by means of, e.g., a luer connector 122, so that the platelet-rich plasma may be directly injected into the patient.

In use, the kit 100 is mounted to a hardware component that includes drive assemblies for the spinning membrane separators, pumps and valve actuators for flowing blood through the kit during processing, and a controller for operating the system within pre-programmed and/or operator-specified parameters. As illustrated, a pump 126 is provided for flowing whole blood from the collection container 110 through the inlet line 106 to the first stage separator 102. If the collection container 110 comprises a syringe, the pump 126 preferably comprises a syringe pump that depresses the syringe plunger at a controlled rate. A pump 128 is also associated with the red blood cell line 112 for flowing separated red blood cells from the first stage separator 102 to the red blood cell waste container 114. Pump 128 is preferably a peristaltic pump, although it, too, may be a syringe pump. A pump 130 is provided for flowing platelet-rich plasma from the second stage separator 104 into the reinfusion container 124. If the reinfusion container 124 is a syringe, the pump 130 may also be a syringe pump that withdraws the plunger from the syringe at a controlled rate.

Figure 4:
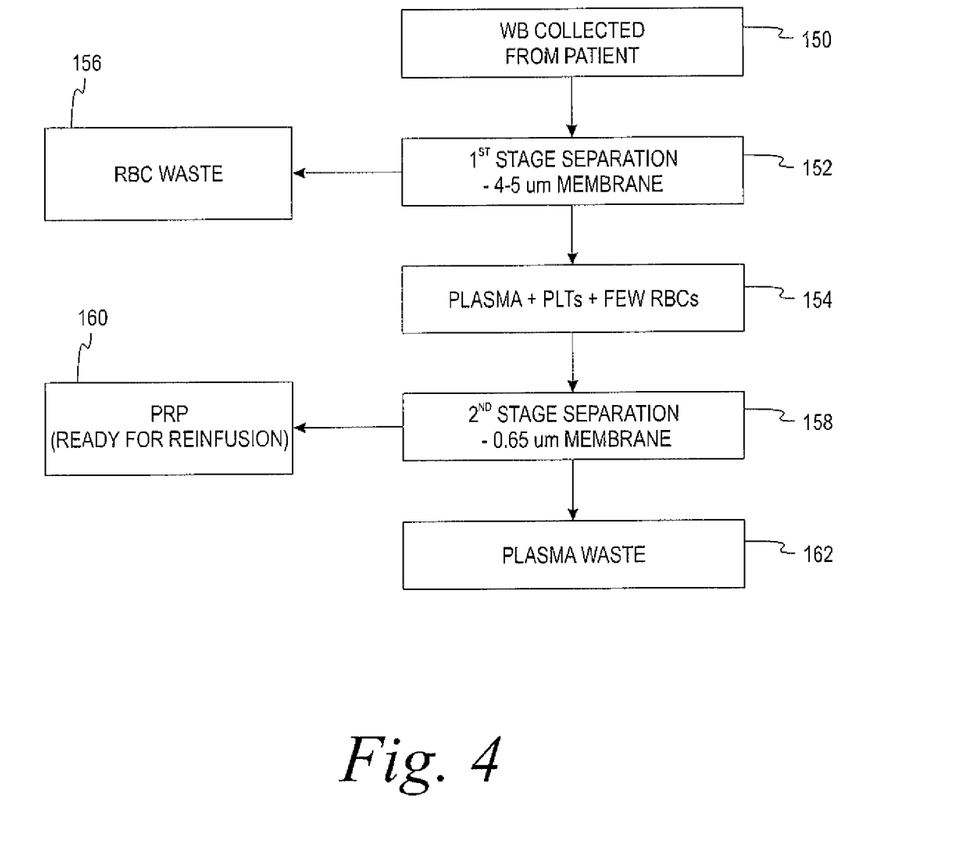
FIG. 4 is a flow chart showing a method for isolating platelet-rich plasma in accordance with the present disclosure.

The basic steps of a method for producing platelet-rich plasma in accordance with the present disclosure are shown schematically in FIG. 4. First, whole blood is collected from the patient (Box 150). This is preferably done by using a syringe to draw whole blood from the patient. Typically, 60 ml of whole blood is drawn. The syringe is then connected to the inlet line 106 via the luer connector 108 so that the whole blood may be flowed to the first stage spinning membrane separator 102 (Box 152).

The membrane in first stage separator 102 then permits plasma, platelets, and a minor amount of red blood cells (i.e., those smaller than 4-5 um pores for the membrane in the first stage separator) to pass therethrough (Box 154), while retaining the majority of red blood cells (Box 156).

The retained red blood cells are removed from the separator 102 through the red blood cell line 112 and flowed into the waste container 114 via the pump 128. The rate of removal of waste red blood cells is typically very slow, depending on the concentration factor of the red blood cells. For example, if the concentration factor of red blood cells to plasma is 10:1, a typical flow rate of whole blood into the separator 102 would be 30 ml/min, and 3 ml/min for the flow of red blood cells through the red blood cell line 112, leaving a flow rate of 27 ml/min for the plasma and platelets flowing out of the separator 102 through the in process line 116.

The platelets flowing through the in process line 116 are then further concentrated by means of the second stage separator 104 (Box 158), which removes most of the remaining plasma. As the plasma passes through the membrane in the second stage separator 104, concentrated platelets are slowly removed from the second stage separator (Box 160) through the platelet-rich plasma line 122 and into the reinfusion container 124 by means of the pump 130, while the separated plasma is flowed into the waste container 120 (Box 162). The differential between the flow rate of plasma and platelets into the separator 104 and the rate at which the pump 130 removes platelet-rich plasma from the separator 104 is the rate at which plasma is filtered out.

Second stage separation is complete once the reinfusion container 124 is filled with a high concentration of platelets suspended in a small amount of plasma. The reinfusion container 124 will also likely contain a very small amount of red blood cells that were passed through the membrane of the first stage separator 102, which is acceptable under current practices. The reinfusion container 124 may then be detached from the platelet-rich plasma line 122 via the luer connector 126. If the reinfusion container 124 is a syringe, a needle may be attached to facilitate prompt injection of platelet-rich plasma back into the patient.

Figure 5:
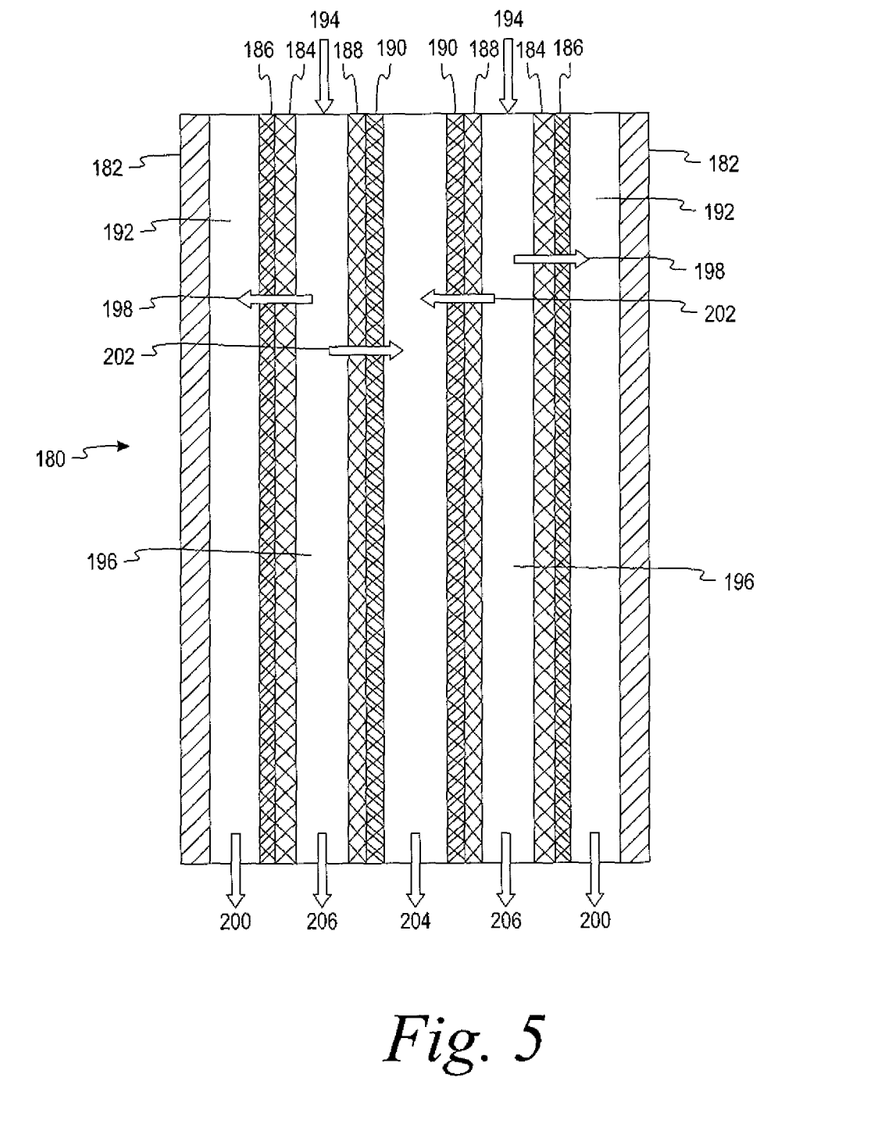
FIG. 5 is a partial cross sectional view of a unitary two-stage spinning membrane separator that may be used in connection with the systems and methods described herein.

The kit and method described above utilize a distinct spinning membrane separator for each stage. However, the two separators may be combined within a single housing in which the filter membrane and support for the second stage is mounted interior of the filter membrane and support for the first stage. With reference to FIG. 5, a partial cross sectional view of a unitary two stage spinning membrane separator 180 is seen. The separator 180 includes a housing 182 that encloses both the first stage filter membrane 188 and support 190 and the second stage filter membrane 184 and support 186. As noted above, the filter membrane 188 for the first stage separation of red blood cells typically has an average pore size of from approximately 4 um to 5 um, while the second stage filter membrane 184 for separating platelet rich plasma from plasma typically has an average pore size of from approximately 0.65 um to 0.8 um. The construction of the membranes and their supports is as described above, and while the first stage membrane/support is interior of the second stage membrane/support in the FIG. 5 embodiment, this could be reversed, with the second stage membrane/support being interior of the first stage membrane/support.

Returning to FIG. 5, a first gap 196 is formed between the two membranes/supports, a second gap 192 is formed between the housing 182 and the second stage membrane and support 184/186, and a central flow path is defined by the interior of the first stage membrane and support 188/190 The filter membrane 188 and support 190 for the first stage is rotatable relative to the housing while the filter membrane 184 and support 186 for the second stage are stationary, so that Taylor vortices may be formed in the gap 196, During first stage separation, whole blood is flowed into the gap 196, as indicated by arrows 194. Fluid is prevented from flowing through the second stage membrane and support 184/186 (by, e.g., closing a valve, clamping or otherwise occluding the flow path external to the housing 182 that is in fluid communication with the gap 192), thus causing the red blood cells in the gap 196 to be retained in the gap 196 and then exited from the housing through an outlet (as indicated by arrow 206) to a waste container. Simultaneously, the plasma, platelets and a few remaining red blood cells flow through the first stage membrane and support 188/190 (as indicated by arrows 202) and out of the housing 182 through an outlet (as indicated by arrow 204) to an in-process container.

During the second stage of separation, the plasma, platelets and remaining red blood cells are flowed from the in-process bag into the gap 196 (as indicated again by arrows 194). Fluid is prevented from flowing through the first stage membrane and support 188/190 (by, e.g., closing a valve, clamping or otherwise occluding the flow path external to the housing 182 that is in fluid communication with the central flow path), thus causing the platelet poor plasma to flow through the second stage membrane and support 184/186 into the gap 192 (as indicated by arrows 198) and out of the housing through an outlet (as indicated by arrows 200) to a waste container, while the platelet rich plasma is retained in the gap 196 and then exited from the housing through an outlet (as indicated by arrow 206) to a final product container (preferably a syringe), It is believed that particular advantages will accrue to the use of the kit and method as described above, especially with respect to current methods that utilize centrifugation for separation and concentration of the platelets. Specifically, it is believed that processing times will be reduced from an average of 15-25 minutes to 5 minutes or less. Further, because a closed system is provided, the platelet-rich plasma may be injected directly into the patient, thus decreasing the likelihood of contamination. In addition, the kit and method described above are relatively simple to use, compared to typical centrifugal separation devices, requiring only that the kit be loaded onto the hardware component.

As set forth above, the disclosed system and method have the following aspects.

In a first aspect, a closed, preassembled and pre-sterilized apparatus for batch processing of blood to provide a concentrated platelet product is provided that comprises a blood inlet; a first gap defined between spaced-apart first inner and first outer relatively rotatable surfaces, the first gap being in fluid communication with the inlet and at least one of the first inner and first outer surfaces comprising a first filter membrane that substantially blocks red blood cells from passing therethrough, while allowing platelets and plasma to pass therethrough; and a second gap defined between spaced-apart second inner and second outer relatively rotatable surfaces, at least one of the second inner and second outer comprising a second filter membrane that substantially blocks platelets from passing therethrough while allowing plasma to pass therethrough. The apparatus is configured so that the second gap receives plasma and platelets passing through the first filter membrane, and includes a drive assembly for causing relative rotational movement between the first inner and first outer surfaces and between the second inner and second outer surfaces, such that plasma and platelets pass through the first filter membrane and plasma passes through the second filter membrane to provide a concentrated platelet product in the second gap. An outlet communicating with the second gap is provided for withdrawing concentrated platelet product from the second gap.

In a related aspect, the inlet comprises a connector for attaching a collection container thereto and the outlet comprises a removably connected reinfusion container.

In a further aspect, the first filter membrane has an average pore size of from 4 um to 5 um and the second filter membrane has an average pore size of approximately 0.65 um.

In another aspect, the first inner relatively rotatable surface of the first gap comprises the second outer relatively rotatable surface of the second gap.

It is also an aspect of the present disclosure to provide an integrated single-use kit forming a closed system for processing whole blood to produce platelet rich plasma. The kit comprises a two stage spinning membrane separator comprising a first stage for receiving whole blood and separating substantially all red blood cells from plasma and platelets, and a second stage in fluid communication with the first stage for further separating platelet rich plasma from plasma. An inlet line is provided for flowing whole blood to the first stage of the separator, and a first waste container in fluid communication with the first stage of the separator is provided for receiving separated red blood cells. A second waste container in fluid communication with the second stage of the separator is provided for receiving separated plasma, and an outlet line in fluid communication with the second stage of the separator is provided for receiving platelet rich plasma. A reinfusion container is removably connected to the outlet line for receiving platelet rich plasma from the second stage of the separator.

In a related aspect, the inlet line further comprises a connector for attaching a collection container thereto. In addition, the reinfusion container may comprise a syringe for withdrawing platelet rich plasma from the second stage of the two stage spinning membrane separator through the outlet line and into the syringe.

In a further aspect, the two stage separator comprises first and second spinning membrane separators, each having an inlet and first and second outlets, the first outlet of the first spinning membrane separator being in fluid communication with the first waste container and the second outlet being in fluid communication with the inlet of the second spinning membrane separator, the first outlet of the second spinning membrane separator being in fluid communication with the outlet line and the second outlet being in fluid communication with the second waste container.

In a further aspect, the two stage separator alternatively comprises a first stationary membrane separator and a second spinning membrane separator mounted interior of the first stationary membrane separator. More specifically, a two-stage system for filtering a cellular suspension is provided that comprises a stationary housing having an inner wall defining a hollow interior; a first generally cylindrical filter membrane and substrate having a hollow interior rotatably fixed relative to the housing and spaced from the inner wall of the housing to define a first gap therebetween; a second generally cylindrical filter membrane and substrate having a hollow interior mounted interior of the first filter membrane and substrate and for rotation relative to the housing and first filter membrane and substrate, the second filter membrane and substrate being spaced relative to the first filter membrane and substrate to define a second gap therebetween; with the housing further having inlet in fluid communication with the second gap and first, second, and third outlets in fluid communication with the first gap, second gap, and hollow interior of the second filter membrane and substrate, respectively; and a motor coupled to the second filter membrane and substrate for rotating the second filter membrane and substrate relative to the housing and first filter membrane and substrate at a rate sufficient to establish Taylor vortices in the second gap. Further, the system preferably further comprises selectively controllable valves or clamps associated with each of the first, second, and third outlets of the housing for controlling the direction of flow through the filter membranes.

In another aspect, a method for producing platelet rich plasma for reinfusion to a donor using the kit of described above is provided. The method includes the steps of obtaining whole blood from the donor in a collection container; connecting the collection container to the inlet line; flowing whole blood from the collection container through the inlet line to the first stage of the two stage spinning membrane separator; separating red blood cells from platelets and plasma in the first stage; flowing separated platelets and plasma from the first stage to the second stage of the spinning membrane separator; separating platelet rich plasma from plasma in the second stage of the two stage spinning membrane separator; flowing the platelet rich plasma from the second stage of the spinning membrane separator through the outlet line to the reinfusion container; and disconnecting the reinfusion container from the outlet line.

In another aspect of the method, the collection container comprises a first syringe associated with a first syringe pump for expressing the whole blood from the first syringe to the first stage of the two stage spinning membrane separator, and the reinfusion container comprises a second syringe associated with a second syringe pump for withdrawing platelet rich plasma from the second stage of the two stage spinning membrane separator through the outlet line and into the second syringe.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An integrated single-use kit forming a closed system for processing whole blood to produce platelet rich plasma comprising:
   a two stage spinning membrane separator comprising a housing, first and second concentric, inner and outer membranes mounted interior of the housing, one of the membranes being rotatable relative to the housing and the other of the membranes being fixed relative to the housing, one of the membranes for separating substantially all red blood cells from plasma and platelets, and the other of the membranes for further separating platelet rich plasma from plasma, a central flow path interior of the inner membrane, an outer flow path defined by the housing and the outer membrane, and a gap defined between the inner membrane and the outer membrane;

an inlet line for flowing whole blood to the gap of the separator during a first stage of separation and to flow plasma and platelets separated from the whole blood during the first stage of separation back into the gap during a second stage of separation;

a first waste container in fluid communication with the gap for receiving separated red blood cells;

a second waste container in fluid communication with one of the central flow path and the outer flow path for receiving separated plasma;

an outlet line in fluid communication with the gap for receiving platelet rich plasma separated in the second stage of separation; and a reinfusion container removably connected to the outlet line for receiving platelet rich plasma from the gap of the separator.

2. The kit of claim 1, wherein the inlet line further comprises a connector for attaching a collection container thereto.

3. The kit of claim 1 wherein the reinfusion container comprises a syringe for withdrawing platelet rich plasma from the gap of the two stage spinning membrane separator through the outlet line and into the syringe.

4. The kit of claim 1, wherein one of the inner and outer membranes comprises a filter membrane having an average pore size of from 4 um to 5 um and the other of the inner and outer membranes comprises a filter membrane having an average pore size of approximately 0.65 um.

5. The kit of claim 1 wherein the inner membrane is rotatable relative to the housing and the outer membrane is fixed relative to the housing.

6. A method for producing platelet rich plasma for reinfusion to a donor using the kit of claim 1, comprising:
    obtaining whole blood from the donor in a collection container;
    connecting the collection container to the inlet line;
    flowing whole blood from the collection container through the inlet line to the first stage of the two stage spinning membrane separator;
    separating red blood cells from platelets and plasma in the first stage;
    flowing separated platelets and plasma from the first stage to the second stage of the spinning membrane separator;
    separating platelet rich plasma from plasma in the second stage of the two stage spinning membrane separator;
    flowing the platelet rich plasma from the second stage of the spinning membrane separator through the outlet line to the reinfusion container; and
    disconnecting the reinfusion container from the outlet line.

7. The method of claim 6 wherein the collection container comprises a first syringe associated with a first syringe pump for expressing the whole blood from the first syringe to the first stage of the two stage spinning membrane separator, and the reinfusion container comprises a second syringe associated with a second syringe pump for withdrawing platelet rich plasma from the second stage of the two stage spinning membrane separator through the outlet line and into the second syringe.

8. A two-stage system for filtering a cellular suspension, comprising:
    A spinning membrane separator in accordance with claim 1; and
    a motor coupled to the inner membrane for rotating the inner membrane relative to the housing and outer membrane at a rate sufficient to establish Taylor vortices in the gap.

9. The system of claim 8 further comprising selectively controllable valves for controlling the direction of flow through the inner and outer membranes.

10. The kit of claim 5 wherein the inner membrane substantially blocks red blood cells from passing therethrough, while allowing platelets and plasma to pass therethrough and the outer membrane substantially blocks platelets from passing therethrough while allowing plasma to pass therethrough.

11. The kit of claim 10 wherein the inner membrane has an average pore size of from 4 um to 5 um and the outer membrane has an average pore size of from approximately 0.65 um to 0.8 um.

12. The kit of claim 5 wherein the reinfusion container comprises a syringe for withdrawing platelet rich plasma from the gap of the two stage spinning membrane separator through the outlet line and into the syringe.

13. The kit of claim 5 wherein the inlet line further comprises a connector for attaching a collection container thereto.

14. The kit of claim 5 wherein the outer membrane substantially blocks red blood cells from passing therethrough, while allowing platelets and plasma to pass therethrough and the inner membrane substantially blocks platelets from passing therethrough while allowing plasma to pass therethrough.

15. The kit of claim 1 wherein the outlet line is configured to flow the red blood cells separated from the whole blood during the first stage of separation to the first waste container and to flow the platelet rich plasma separated from the plasma and platelets during the second stage of separation to the reinfusion container, and the kit further comprises a second outlet line in fluid communication with one of the central flow path and the outer flow path for flowing the plasma separated from the plasma and platelets during the second stage of separation to the second waste container.

* * * * *